United States Patent
Iwai et al.

(10) Patent No.: US 10,859,514 B2
(45) Date of Patent: Dec. 8, 2020

(54) X-RAY INSPECTION DEVICE

(71) Applicant: ISHIDA CO., LTD., Kyoto (JP)

(72) Inventors: Atsushi Iwai, Ritto (JP); Hikari Harada, Ritto (JP); Futoshi Yurugi, Ritto (JP); Takashi Kabumoto, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 307 days.

(21) Appl. No.: 15/551,382

(22) PCT Filed: Feb. 3, 2016

(86) PCT No.: PCT/JP2016/053239
§ 371 (c)(1),
(2) Date: Aug. 16, 2017

(87) PCT Pub. No.: WO2016/132907
PCT Pub. Date: Aug. 25, 2016

(65) Prior Publication Data
US 2018/0027640 A1 Jan. 25, 2018

(30) Foreign Application Priority Data
Feb. 20, 2015 (JP) .................................. 2015-032301

(51) Int. Cl.
*G01N 23/083* (2018.01)
*G06F 1/26* (2006.01)
(Continued)

(52) U.S. Cl.
CPC .......... *G01N 23/083* (2013.01); *G01N 23/18* (2013.01); *G06F 1/263* (2013.01); *G06F 1/30* (2013.01);
(Continued)

(58) Field of Classification Search
CPC .......... H05G 1/10; G01N 23/04; G01N 23/18; H02J 9/06
See application file for complete search history.

(56) References Cited

U.S. PATENT DOCUMENTS

RE35,025 E * 8/1995 Anderton ............ H05G 1/10
320/DIG. 10
2002/0052695 A1 5/2002 Arake et al.
(Continued)

FOREIGN PATENT DOCUMENTS

CN 2167366 Y 6/1994
CN 101652655 A 2/2010
(Continued)

OTHER PUBLICATIONS

Tamai et al.—WO 2009-101772 A1—English Translation obtained from Google Patents on May 24, 2019 (Year: 2019).*
(Continued)

*Primary Examiner* — David P Porta
*Assistant Examiner* — Jeremy S Valentiner
(74) *Attorney, Agent, or Firm* — Global IP Counselors, LLP

(57) ABSTRACT

An X-ray inspection apparatus includes an X-ray source that radiates X-rays to a product, an X-ray detection unit that detects X-rays penetrating the product, and an uninterruptible power supply that supplies electric power during an electric power failure. The uninterruptible power supply is not electrically connected to the X-ray source.

4 Claims, 3 Drawing Sheets

(51) Int. Cl.
*H05G 1/10* (2006.01)
*G06F 1/30* (2006.01)
*G01N 23/18* (2018.01)
*H02J 9/06* (2006.01)

(52) U.S. Cl.
CPC ............... *H02J 9/06* (2013.01); *H05G 1/10* (2013.01); *A61B 2560/0214* (2013.01); *G01N 2223/304* (2013.01); *G01N 2223/32* (2013.01); *G01N 2223/643* (2013.01)

(56) References Cited

U.S. PATENT DOCUMENTS

| | | | |
|---|---|---|---|
| 2004/0252613 A1* | 12/2004 | Iwakiri | G03B 42/02 369/53.12 |
| 2006/0103540 A1* | 5/2006 | Rutter | G08B 17/00 340/628 |
| 2008/0192897 A1 | 8/2008 | Piorek et al. | |
| 2010/0187430 A1* | 7/2010 | Yoshimuta | A61B 6/032 250/370.09 |
| 2010/0230606 A1* | 9/2010 | Liu | G01T 1/175 250/370.04 |
| 2013/0099756 A1 | 4/2013 | Mohr et al. | |
| 2013/0223596 A1* | 8/2013 | Kojima | H05G 1/10 378/102 |
| 2015/0006943 A1* | 1/2015 | Suzuki | G06F 1/263 713/340 |

FOREIGN PATENT DOCUMENTS

| | | | | |
|---|---|---|---|---|
| CN | 103155350 A | | 6/2013 | |
| EP | 2169430 A1 | | 3/2010 | |
| JP | 2002-139504 A | | 5/2002 | |
| JP | 2002-372505 A | | 12/2002 | |
| JP | 3349555 B2 | | 9/2003 | |
| JP | 3449555 B2 | | 9/2003 | |
| JP | 2004-020297 A | | 1/2004 | |
| JP | 2004020297 A | * | 1/2004 | ............ G01N 23/04 |
| JP | 2005-118348 A | | 5/2005 | |
| JP | 2009-005451 A | | 1/2009 | |
| JP | WO2009011027 A1 | | 9/2010 | |
| JP | 4686080 B2 | | 5/2011 | |
| WO | WO-2009101772 A1 | * | 8/2009 | ............ G01N 23/04 |

OTHER PUBLICATIONS

Totani—JP 2004-020297 A—English Translation Google Patents obtained Mar. 31, 2020 (Year: 2020).*
Extended European Search Report of the corresponding European Patent Application No. 16752294.5, dated Sep. 25, 2018.
Translation of the Written Opinion of the International Searching Authority, dated Apr. 5, 2016.

* cited by examiner

X-RAY INSPECTION DEVICE

CROSS-REFERENCE TO RELATED APPLICATIONS

This U.S. National Stage application of PCT/JP2016/053239 claims priority under 35 U.S.C. § 119(a) to Japanese Patent Application No. 2015-032301, filed in Japan on Feb. 20 2015 the entire contents of which are hereby incorporated herein by reference.

TECHNICAL FIELD

An aspect of the present invention relates to an X-ray inspection apparatus.

BACKGROUND ART

An X-ray inspection apparatus including an X-ray source that radiates X-rays to a product and an X-ray detection unit that detects X-rays penetrating the product is known (e.g., see Japanese Patent No. 4686080).

SUMMARY OF INVENTION

Technical Problem

In the above-described X-ray inspection apparatus, an external power supply is normally used as an electric power supply. For example, if a temporary electric power failure or the like occurs in a state in which the external power supply is unstable, an operation of the X-ray inspection apparatus may be affected. Thus, an uninterruptible power supply may connect to the X-ray inspection apparatus. However, if the electric power required by the X-ray inspection apparatus increases, there is a problem in that a size of the uninterruptible power supply increases because the electric power to be supplied from the uninterruptible power supply to the X-ray inspection apparatus increases during an electric power failure.

Therefore, an objective of an aspect of the present invention is to provide an X-ray inspection apparatus capable of suppressing an increase in a size of an uninterruptible power supply.

Solution to Problem

According to an aspect of the present invention, there is provided an X-ray inspection apparatus including: an X-ray source that radiates X-rays to a product; an X-ray detection unit that detects X-rays penetrating the product; and an uninterruptible power supply that supplies electric power during an electric power failure of an external power supply, wherein the UPS is not electrically connected to the X-ray source.

In the X-ray inspection apparatus, the uninterruptible power supply is not electrically connected to the X-ray source. Thereby, electric power is not supplied from the uninterruptible power supply to the X-ray source even during an electric power failure. Therefore, it is possible to suppress an increase in a size of the uninterruptible power supply because it is possible to suppress electric power to be supplied by the uninterruptible power supply during the electric power failure.

The X-ray inspection apparatus according to the aspect of the present invention may further include a processing unit that performs an inspection of the product based on an electric signal output from the X-ray detection unit and records inspection information regarding the inspection, wherein the uninterruptible power supply is electrically connected to the processing unit. In this case, electric power is supplied from the uninterruptible power supply to the processing unit which records the inspection information regarding the inspection of the product, during an electric power failure. Therefore, it is possible to prevent the inspection information from being lost even when an electric power failure occurs.

In the X-ray inspection apparatus according to the aspect of the present invention, the processing unit may record first information relating to the inspection, from the inspection information in a first storage area that is a temporary storage area, and the processing unit may record second information regarding a result of the inspection, from the inspection information in a second storage area that is a permanent storage area. In this case, for example, it is easy to add new first information to the first information already stored in the first storage area by recording the first information relating to the inspection, from the first storage area (for example, running onto a RAM). Also, it is possible to reliably record the second information by recording the second information regarding the result of the inspection, from the second storage area (for example, an HDD).

In the X-ray inspection apparatus according to the aspect of the present invention, the processing unit may associate a type of a malfunction with operation states of the X-ray source and the X-ray detection unit in recording the type of the malfunction and the operation states when the malfunction occurs in cases where the malfunction occurs in the X-ray source or the X-ray detection unit, the malfunction occurs in the uninterruptible power supply, and the electric power failure occurs as the malfunction of the external power supply. In this case, it is possible to appropriately cope with the malfunction in accordance with the type of the malfunction occurred, because the type of the malfunction and the operation state of the X-ray source or the X-ray detection unit are associated with each other in recording the type of the malfunction and the operation state when the malfunction occurs, in a case where the malfunction occurs. Also, it is possible to perform reliable recording in the processing unit even during an electric power failure of the external power supply, because the uninterruptible power supply is electrically connected to the processing unit.

Effects of Invention

According to an aspect of the present invention, it is possible to provide an X-ray inspection apparatus capable of suppressing an increase in a size of an uninterruptible power supply.

DESCRIPTION OF EMBODIMENTS

Hereinafter, preferred embodiments of an aspect of the present invention will be described in detail with reference to the accompanying drawings. The same reference signs are assigned to the same or corresponding elements in the description of the drawings and redundant description thereof will be omitted.

[X-ray Inspection Apparatus]

Figure 1:
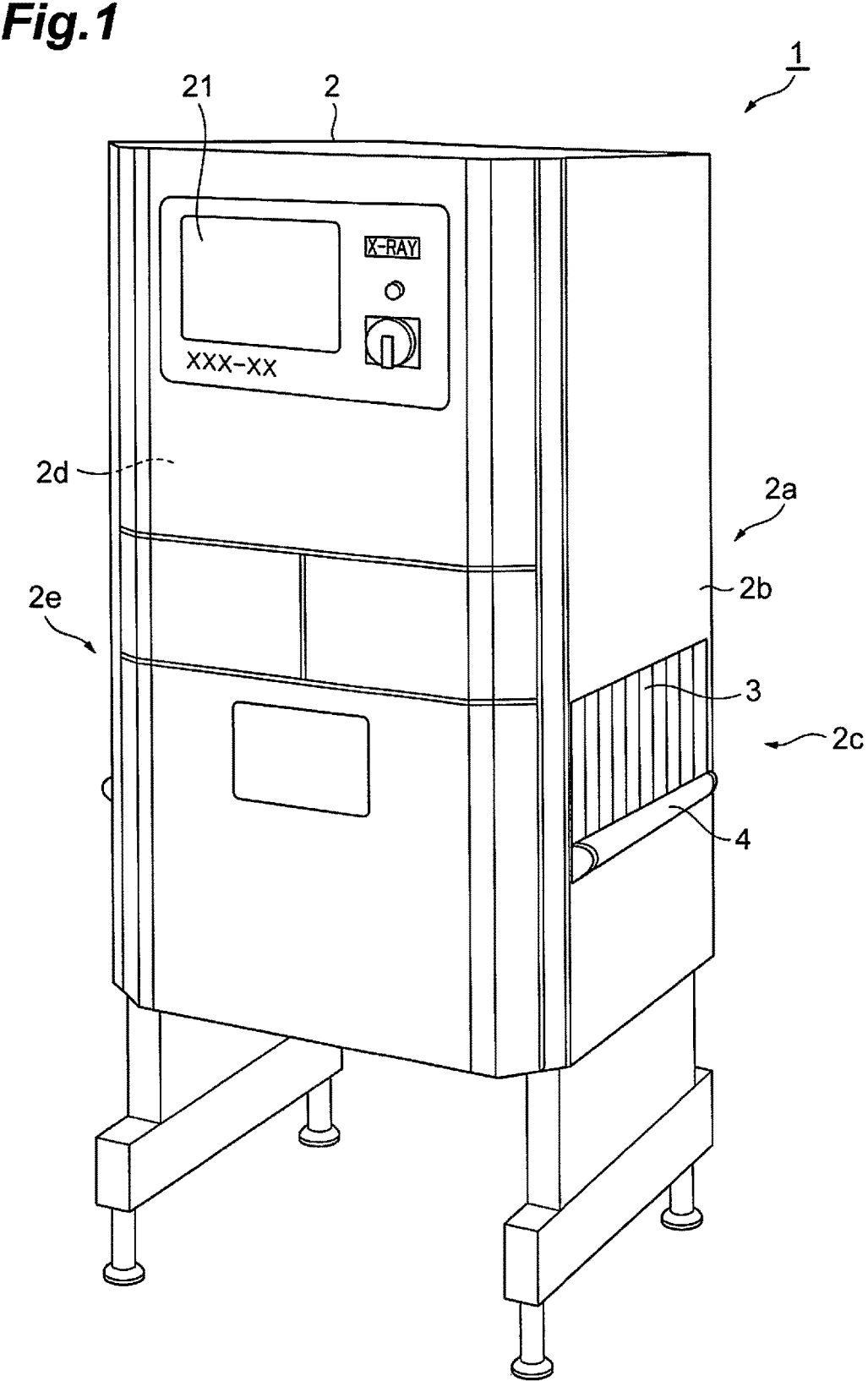
FIG. 1 is a perspective view of an X-ray inspection apparatus according to an embodiment of an aspect of the present invention.
Figure 2:
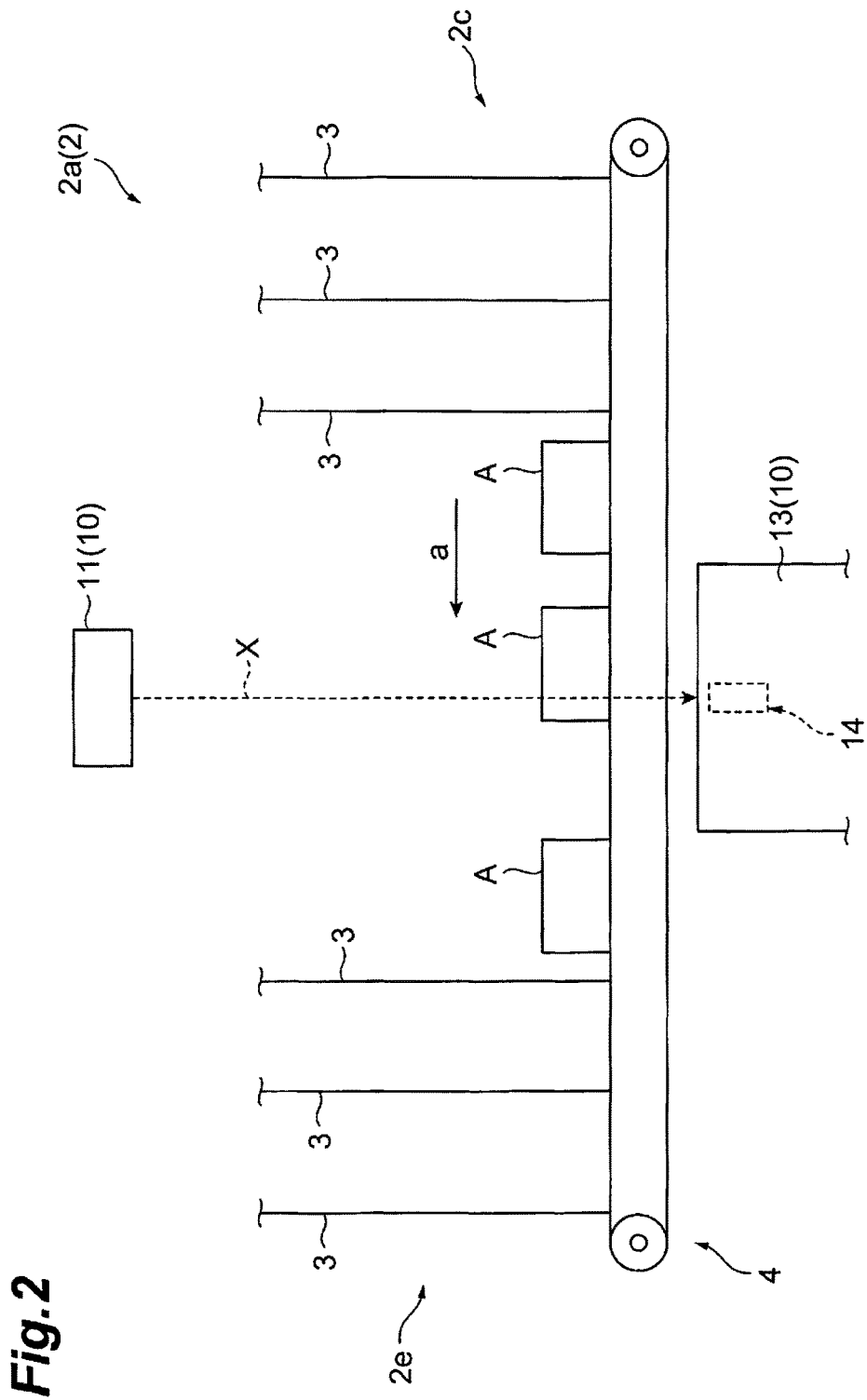
FIG. 2 is a side view of an internal configuration of the X-ray inspection apparatus of FIG. 1.

As illustrated in FIGS. 1 and 2, an X-ray inspection apparatus 1 radiates X-rays to a product while conveying the product and detects X-rays in order to inspect whether or not a foreign object is mixed into the product. The X-ray inspection apparatus 1 includes a main body 2, an X-ray shielding curtain 3, and a carrying conveyor 4. The X-ray inspection apparatus 1 inspects whether or not a foreign object is mixed into the product A or the like while the product A is conveyed in a conveying direction a.

The main body 2 includes an inspection chamber 2a formed in a box shape. A carry-in port 2c through which the product A passes is provided in an upstream side wall 2b in the conveying direction a. A carry-out port 2e through which the product A passes is provided in a downstream side wall 2d in the conveying direction a. The X-ray shielding curtain 3 is provided at each of the carry-in port 2c and the carry-out port 2e. The X-ray shielding curtain 3 prevents scattered X-rays from leaking outside the inspection chamber 2a.

A general flat belt conveyor is used for the carrying conveyor 4. Both ends of the carrying conveyor 4 protrude from the carry-in port 2c and the carry-out port 2e of the inspection chamber 2a, respectively. The carrying conveyor 4 receives the product A before an inspection from a carry-in conveyor (not illustrated) on an upstream side in the conveying direction a. The carrying conveyor 4 carries the product A inside the inspection chamber 2a from the carry-in port 2c. The carrying conveyor 4 carries the product A outside the inspection chamber 2a from the carry-out port 2e. The carrying conveyor 4 transfers the inspected product A to a carry-out conveyor (not illustrated) on a downstream side in the conveying direction a. Also, a sorting function for the product A may be provided in the carry-out conveyor.

Figure 3:
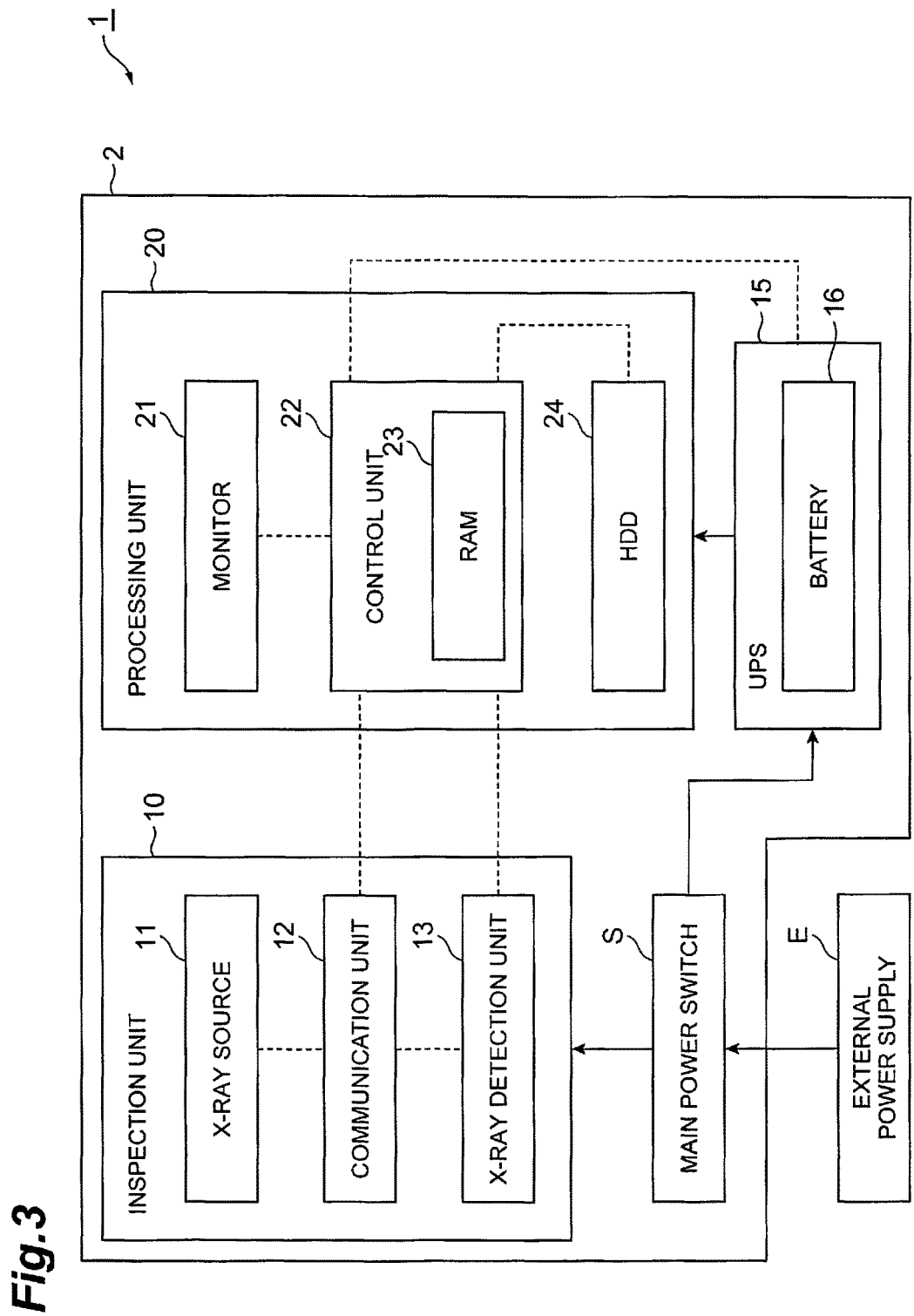
FIG. 3 is a block diagram of the X-ray inspection apparatus of FIG. 1.

As illustrated in FIG. 3, the X-ray inspection apparatus 1 includes an inspection unit 10, a processing unit 20, an uninterruptible power supply (UPS) 15, and a main power switch S. In the following description, an electrical connection relationship between components related to the supply of electric power indicated by a solid-line arrow in FIG. 3 is referred to as "electrically connected" and an electrical connection relationship between components other than the supply of electric power indicated by a broken line in FIG. 3 is referred to as "electrically connected as by an electric signal."

The inspection unit 10 includes an X-ray source 11, a communication unit 12, and an X-ray detection unit 13. As illustrated in FIGS. 2 and 3, the X-ray source 11 is arranged above the inspection chamber 2a in the main body 2. The X-ray source 11 radiates X-rays to the product A carried in the inspection chamber 2a while forming an X-ray radiation area via a slit mechanism (not illustrated) or the like. The X-ray source 11 is electrically connected as by an electric signal to the communication unit 12. If a malfunction occurs in the X-ray source 11, the X-ray source 11 transmits information to the communication unit 12 indicating that a malfunction has occurred. The X-ray source 11 transmits information regarding an operation state of the X-ray source 11 to the communication unit 12.

The communication unit 12 is an I/O board that intensively performs communication related to an input and output of information between the inspection unit 10 and the processing unit 20. The communication unit 12 is electrically connected as by an electric signal to a control unit 22 to be described below. The communication unit 12 communicates with the control unit 22 at a certain periods (for example, every 100 ms). If a malfunction of the X-ray source 11 or a malfunction of the X-ray detection unit 13 occurs, the communication unit 12 transmits information to the control unit 22 indicating that a malfunction has occurred. The communication unit 12 transmits information regarding operation states transmitted from the X-ray source 11 and the X-ray detection unit 13 to the control unit 22.

The X-ray detection unit 13 is arranged below the inspection chamber 2a in the main body 2 so that the X-ray detection unit 13 faces the X-ray source 11. The X-ray detection unit 13 includes a line sensor 14. The line sensor 14 includes a plurality of pixels arranged in a row in a width direction in the conveying direction a (a direction perpendicular to the conveying direction a and a vertical direction). The X-ray detection unit 13 detects X-rays penetrating the product A. The X-ray detection unit 13 is electrically connected as by an electric signal to the processing unit 20 (a control unit 22). When the product A passes through the X-ray radiation area, the X-ray detection unit 13 acquires a detection signal at a predetermined timing. The X-ray detection unit 13 outputs the electric signal to the control unit 22 related to the detection signal. That is, the inspection unit 10 outputs an electric signal for inspecting the product A to the control unit 22.

The X-ray detection unit 13 is electrically connected as by an electric signal to the communication unit 12. If a malfunction occurs in the X-ray detection unit 13, the X-ray detection unit 13 transmits information to the communication unit 12 indicating that a malfunction has occurred. The X-ray detection unit 13 transmits information regarding the operation state of the X-ray detection unit 13 to the communication unit 12.

The UPS 15 has a battery 16 and is a device that supplies electric power of the battery 16 during an electric power failure in the external power supply E. The UPS 15 is electrically connected as by an electric signal to the control unit 22 to be described below. The UPS 15 communicates with the control unit 22 at a certain periods (for example, every 10 s). The UPS 15 transmits information regarding the state of the UPS 15 to the control unit 22 at a certain periods or in response to an inquiry from the control unit 22. The state of the UPS 15 includes a voltage of the external power supply E, the presence or the absence of an electric power failure in the external power supply E, and the remaining amount of the battery 16.

The processing unit 20 inspects the product A based on the electric signal received from the X-ray detection unit 13, and records inspection information regarding the inspection. The processing unit 20 includes a monitor 21, the control unit 22, a random access memory (RAM) (a first storage area) 23, and a hard disk drive (HDD) (a second storage area) 24.

The monitor 21 is provided in an upper part of a front face portion of the main body 2 (see FIG. 1). The monitor 21 is a display unit that displays an operation state of the X-ray inspection apparatus 1, an X-ray image of the product A, an inspection result, and the like. The monitor 21 has a touch panel function and performs display for an input operation. The input operation includes an input operation of a reservation setting, a start and a stop operation of the inspection unit 10, and other inspection management operations (a password setting and the like). The reservation setting is a setting related to the operation state of the inspection unit 10 to be set before or during the inspection. The monitor 21 is electrically connected as by an electric signal to the control unit 22, and transmits operation information related to the input operation to the control unit 22.

The operation state of the inspection unit 10 includes operation states of the X-ray source 11 and the X-ray detection unit 13. The operation state of the X-ray source 11 is, for example, the intensity of X-rays output by the X-ray source 11. The intensity of the X-rays may be acquired based on, for example, a voltage and a current in the X-ray source 11. The operation state of the X-ray detection unit 13 is, for example, the detecting intensity of X-rays detected by the X-ray detection unit 13. The detected intensity of the X-rays may be acquired based on, for example, an output of the line sensor 14. Also, the operation state of the inspection unit 10 includes an operating state of the inspection unit 10. The operating state of the inspection unit 10 includes, for example, a type and properties of the product A (a length along the conveying direction a or the like), a conveying speed of the carrying conveyor 4, set values of the voltage and current in the X-ray source 11, a sensitivity of the line sensor 14, inspection standards, and the like.

The control unit 22 comprehensively controls processing related to the inspection in the processing unit 20. The control unit 22 performs image processing on an electric signal related to the X-ray image of the product A output from the X-ray detection unit 13, thereby inspecting the mixing of a foreign object or the like for the product A. The control unit 22 includes the RAM 23 and includes a central processing unit (CPU) and a read only memory (ROM).

The control unit 22 records the inspection information regarding the inspection of the product A. The control unit 22 records (runs) first information relating to the inspection, from the inspection information onto the RAM 23. The RAM 23 is a temporary storage area. The control unit 22 can edit the first information recorded on the RAM 23 accordingly. For example, the control unit 22 can perform editing of adding new first information to the first information already stored in the first storage area.

The first information includes the operation state of the inspection unit 10. Also, the first information includes operation history information (an operation record), NG history information, aggregated data, and information regarding a user, a use date and time, or the like of the X-ray inspection apparatus 1. The operation history information is created by the control unit 22 based on the operation information received from the monitor 21. For example, the operation history information may be a time-series list created by performing editing of adding operation details every time that an operation such as an inspection start, an inspection stop, a setting change, or the like is performed. The NG history information is a time-series list created by performing editing of adding details of each product A having a problem in the inspection result, such as a product having a foreign object or a product having a missing article. The aggregated data is a list for each of a certain period of times created by performing classification by the presence or absence of a foreign object, a missing article, or the like, aggregating the number of products A, and performing editing of adding details.

The control unit 22 records the second information regarding the result of the inspection, from the inspection information on the HDD 24. The HDD 24 is a permanent storage area. The control unit 22 records the second information on the HDD 24 for each inspection of each product A (in real time). The second information includes X-ray image data and inspection result data that are results of inspection of the product A. The inspection result data is details of the inspection result corresponding to the X-ray image data of each product A. The inspection result data includes, for example, a determination result of the inspection (the presence or absence of a foreign object, a missing article, or the like), an inspection date and time, and the like.

The control unit 22 records the first information recorded on the RAM 23 onto the HDD 24, if the operation of the X-ray inspection apparatus 1 is stopped. Also, the control unit 22 records the first information recorded on the RAM 23 onto the HDD 24, if the risk of the X-ray inspection apparatus 1 stopping due to a malfunction occurring. The control unit 22 records (rims) the first information recorded on the HDD 24 onto the RAM 23, if the operation is activated (resumed) after the operation of the X-ray inspection apparatus 1 was stopped. The occurrence of a malfunction includes an occurrence of a malfunction of the inspection unit 10 (that is, a malfunction of the X-ray source 11 or the X-ray detection unit 13), an occurrence of a malfunction of the UPS 15, an occurrence of an electric power failure as a malfunction of the external power supply E, and the like.

The control unit 22 receives information indicating that a malfunction has occurred in the X-ray source 11 or the X-ray detection unit 13 from the communication unit 12 in communication with the communication unit 12 at a certain periods. The control unit 22 transmits information indicating that a malfunction has occurred in the UPS 15 and information indicating that an electric power failure has occurred as a malfunction of the external power supply E from the UPS 15 in accordance with communication with the UPS 15 at a certain periods or with communication in response to an inquiry from the control unit 22.

[Associating Type of Malfunction with Operation State of Inspection Unit in Recording Them]

Here, if a malfunction occurs in the X-ray source 11 or the X-ray detection unit 13, if a malfunction occurs in the UPS 15, and if an electric power failure occurs as a malfunction of the external power supply E, the control unit 22 associates and records the type of malfunction and the operation state of the inspection unit 10 (the X-ray source 11 and the X-ray detection unit 13) when the malfunction occurs. Specifically, the control unit 22 generates, for example, a single file named after a time at which the malfunction occurred. The control unit 22 associates the type of the malfunction with the information regarding the operation state of the inspection unit 10 when the malfunction occurs by indicating these together in this file. The control unit 22 records this file on the HDD 24. Before the occurrence of a malfunction, the control unit 22 runs the information related to the operation state of the inspection unit 10 onto the RAM 23. The control unit 22 utilizes the information regarding the operation state of the inspection unit 10 run onto the RAM 23 when the malfunction occurs as the information related to the operation state of the inspection unit 10 when the malfunction occurs. Consequently, the control unit 22 can associate the type of the malfunction with the operation state of the inspection unit 10 when the malfunction occurs. This information is valuable information for identifying a cause of occurrence of the malfunction.

Examples of the types of malfunction include a malfunction of the inspection unit 10, a malfunction of the UPS 15, an electric power failure as a malfunction of the external power supply E, and the like. The malfunction of the inspection unit 10 includes a malfunction of the X-ray source 11, a malfunction of the communication unit 12, and a malfunction of the X-ray detection unit 13. The malfunction of the X-ray source 11 is, for example, a decrease in the intensity of X-rays output from the X-ray source 11. The malfunction of the communication unit 12 is, for example, inability to communicate related to an input and output of information between the inspection unit 10 and the control unit 22. The malfunction of the X-ray detection unit 13 is, for example, a decrease in the detecting intensity of X-rays detected by the X-ray detection unit 13. The malfunction of the UPS 15 is, for example, deterioration of the battery 16 or inability of the battery 16 to charge of the battery 16. An electric power failure as a malfunction of the external power supply E includes an electric power failure that the supply of electric power from the external power supply E is continuously interrupted (hereinafter simply referred to as a "electric power failure") and an instantaneous electric power failure that the supply of electric power from the external power supply E is instantaneously interrupted.

Also, examples of the operation state of the inspection unit 10 when a malfunction occurs include: a level of an intensity of X-rays output by the X-ray source 11 (a voltage and a current in the X-ray source 11); a level of a detection intensity of X-rays detected by the X-ray detection unit 13; a type of product A to be inspected by the X-ray inspection apparatus 1; a level of a conveying speed of the carrying conveyor 4; and a type of inspection standard, and the like when the malfunction occurs.

[Electric Power Supply Path]

Next, the electric power supply path in the X-ray inspection apparatus 1 will be described with reference to FIG. 3. A main power switch S is a principal electric power switch in the X-ray inspection apparatus 1. The main power switch S is electrically connected to the external power supply E. If the main power switch S is closed, the main power switch S passes a current from the external power supply E. If the main power switch S is open, the main power switch S shuts off the current from the external power supply E. In the following description, it is assumed that the main power switch S is closed.

The inspection unit 10 is not electrically connected to the UPS 15 and is electrically connected to the external power supply E via the main power switch S. That is, the UPS 15 is not connected to supply electric power to the inspection unit 10. Neither electric power from the external power supply E nor electric power from the UPS 15 is supplied to the inspection unit 10 if an electric power failure of the external power supply E occurs. Therefore, electric power is not supplied from the UPS 15 to the X-ray source 11 during an electric power failure of the external power supply E.

On the other hand, the processing unit 20 is electrically connected to the external power supply E via the UPS 15. That is, the UPS 15 is connected to supply electric power to the processing unit 20. The electric power from the battery 16 of the UPS 15 is supplied to the processing unit 20 if an electric power failure of the external power supply E occurs. Therefore, electric power is supplied from the UPS 15 to the processing unit 20 during an electric power failure, which records the inspection information regarding the inspection of the product A.

[Working and Effect]

The X-ray inspection apparatus 1 includes the X-ray source 11 that radiates X-rays to the product A, the X-ray detection unit 13 that detects X-rays penetrating the product A, and the UPS 15 that supplies electric power during an electric power failure. In the X-ray inspection apparatus 1, the UPS 15 is not electrically connected to the X-ray source 11. That is, No electrical connections capable of supplying electric power exist between the X-ray source 11 and the UPS 15. Thus, no electric power is supplied from the UPS 15 to the X-ray source 11 even during an electric power failure. Therefore, an increase in the size of the UPS 15 can be suppressed, because it is possible to suppress the electric power the UPS 15 supplies to the X-ray inspection apparatus 1 during the electric power failure. In particular, if the electric power required by the X-ray source 11 is large, the electric power to be supplied to the X-ray inspection apparatus 1 by the UPS 15 during the electric power failure can be greatly suppressed, so that it is possible to effectively suppress the increase in the size of the UPS 15. The safety of a worker who works in the inspection unit 10 may decrease during the electric power failure, because, for example, an illumination in an installation place of the X-ray inspection apparatus 1 goes off. In this regard, in the X-ray inspection apparatus 1, the safety of the worker can be ensured, because the inspection unit 10 is not electrically connected to the UPS 15.

The X-ray inspection apparatus 1 further includes the processing unit 20 that inspects the product A based on an electric signal output from the X-ray detection unit 13 and records inspection information regarding the inspection. The UPS 15 is electrically connected to the processing unit 20. That is, an electrical connection capable of supplying electric power exists between the processing unit 20 and the UPS 15. Thus, electric power is supplied from the UPS 15 to the processing unit 20 during an electric power failure, which records the inspection information regarding the inspection of the product A. Therefore, even if an electric power failure occurs, it is possible to prevent the inspection information from being lost.

In the X-ray inspection apparatus 1, the processing unit 20 records first information relating to the inspection, from the inspection information onto the RAM 23 that is the temporary storage area. The processing unit 20 records second information regarding the result of the inspection, from the inspection information on the HDD 24 that is the permanent storage area. As described above, by running (recording) the first information relating to the inspection onto the RAM 23, for example, it is easy to add new first information to the first information already stored in the RAM 23. It is possible to reliably record the second information by recording the second information regarding the result of the inspection in the HDD 24. Both the first information (an operation record) relating to the inspection, from the inspection information, and the second information regarding the result of the inspection are permanently recorded and thus protected, because the first information stored in the RAM 23 during the operation of the X-ray inspection apparatus 1 is saved onto the HDD 24 when the operation of the X-ray inspection apparatus 1 is stopped.

In the X-ray inspection apparatus 1, the processing unit 20 associates a type of malfunction with operation states of the X-ray source 11 and the X-ray detection unit 13 in recording the type of malfunction and the operation states when the malfunction occurs in cases where the malfunction occurs in the X-ray source 11 or the X-ray detection unit 13, the malfunction occurs in the UPS 15, and the electric power failure occurs as the malfunction of the external power supply E. In this case, it is possible to appropriately cope with a malfunction in accordance with the type of the malfunction occurred, because the type of malfunction and the operation state of the X-ray source 11 or the X-ray detection unit 13 when the malfunction occurs are associated with each other in recording the type of the malfunction and the operation state when the malfunction occurs in a case where the malfunction occurs. Also, it is possible to perform reliable recording in the processing unit 20 even during an electric power failure of the external power supply E, because the UPS 15 is electrically connected to the processing unit 20.

[Modification]

The X-ray inspection apparatus 1 has been described as an example of an inspection apparatus including the inspection unit 10 and the processing unit 20 in the above-described embodiment. However, it is also possible to make a configuration in which the UPS 15 is not electrically connected to the inspection unit 10 and make a configuration in which the UPS 15 is electrically connected to the processing unit 20 even in another inspection apparatus such as, for example, a metal detector, a near infrared ray inspection apparatus, a weight checker (a weight inspection apparatus), or a seal checker.

The invention claimed is:

1. An X-ray inspection apparatus comprising:
    an X-ray source configured to radiate X-rays to a product;
    an X-ray detection unit configured to detect X-rays penetrating the product;
    a processing unit in communication with the X-ray detection unit;
    an external power supply; and
    an uninterruptible power supply supplying electric power to the processing unit in the event of an electric power failure of the external power supply,
    a main power switch connected to the X-ray source, the external power supply and the uninterruptible power supply, the main power switch being operable to connect and disconnect the external power supply to the X-ray source, and, connect and disconnect the external power supply to the uninterruptible power supply and the processing unit;
    wherein the uninterruptible power supply is not electrically connected to the X-ray source.

2. The X-ray inspection apparatus according to claim 1, further comprising:
    the processing unit configured to perform an inspection of the product based on an electric signal output from the X-ray detection unit, the processing unit being further configured to record inspection information regarding the inspection.

3. The X-ray inspection apparatus according to claim 2, wherein
    the processing unit is configured to record first information relating to the inspection, from the inspection information in a first storage area that is a temporary storage area, and
    wherein the processing unit is configured to record second information regarding a result of the inspection, from the inspection information in a second storage area that is a permanent storage area.

4. The X-ray inspection apparatus according to claim 2, wherein
    the processing unit is configured to associate a type of a malfunction with operation states of the X-ray source and the X-ray detection unit when recording the type of the malfunction and the operation states when the malfunction occurs in cases where the malfunction occurs in the X-ray source or the X-ray detection unit, the malfunction occurs in the uninterruptible power supply, and the electric power failure occurs as the malfunction of the external power supply.

* * * * *